United States Patent [19]

Rosenberger

[11] 4,194,391

[45] Mar. 25, 1980

[54] DEVICE FOR DETERMINING SETTLING RATES OF SOLIDS OR PARTICULATE BEARING LIQUID IN A CONTINUOUS PROCESS OR FLOWING STREAM

[75] Inventor: Roy R. Rosenberger, Wheaton, Ill.

[73] Assignee: Nalco Chemical Company, Oak Brook, Ill.

[21] Appl. No.: 838,752

[22] Filed: Oct. 3, 1977

[51] Int. Cl.² ............................................. G01N 15/04
[52] U.S. Cl. ...................................................... 73/61.4
[58] Field of Search ............. 73/61.4, 61 R; 356/102, 356/208; 346/33 A

[56] References Cited

U.S. PATENT DOCUMENTS

| 2,379,158 | 6/1945  | Kalischer    | 73/61.4 X |
| 2,725,782 | 12/1955 | Worley       | 73/61.4 X |
| 3,261,256 | 7/1966  | Morton, Jr.  | 73/61.4   |
| 3,519,353 | 7/1970  | Franz et al. | 73/61.4 X |
| 3,604,924 | 9/1971  | Standaart    | 73/61.4 UX|
| 3,715,761 | 2/1973  | Drekter et al.| 356/208 X|

FOREIGN PATENT DOCUMENTS

| 604006  | 10/1934 | Fed. Rep. of Germany | 356/208 |
| 2339696 | 2/1975  | Fed. Rep. of Germany | 73/61.4 |
| 2341403 | 2/1975  | Fed. Rep. of Germany | 73/61.4 |
| 488118  | 1/1976  | U.S.S.R.             | 73/61.4 |

Primary Examiner—Gerald Goldberg
Assistant Examiner—Joseph W. Roskos
Attorney, Agent, or Firm—Hill, Van Santen, Steadman, Chiara & Simpson

[57] ABSTRACT

Apparatus and method for determining the settling rate of solids or particulate bearing liquids in a continuous process or flowing stream in which a sample of the material is periodically selected and placed in a chamber which is transparent or has a transparent portion through which a light beam can pass such that a detector detects the amount of light passing through the chamber and the material and wherein the light transmissivity at various times is recorded and used to calculate the partial settling rate, the full settling rate and the percentage of solids or parts per million in the sample.

6 Claims, 2 Drawing Figures

1

DEVICE FOR DETERMINING SETTLING RATES OF SOLIDS OR PARTICULATE BEARING LIQUID IN A CONTINUOUS PROCESS OR FLOWING STREAM

BACKGROUND OF THE INVENTION

1. Field of the Invention

The present invention relates to apparatus and method for measuring settling rates of a solid or particulate bearing liquid in a continuous process of a flowing stream.

2. Description of the Prior Art

Present methods for determining the settling rate of solids or particulate bearing liquid in a continuous process or flowing stream are very laborious and require a great deal of manual labor. The results of such systems are very inaccurate.

SUMMARY OF THE INVENTION

The present invention comprises apparatus and method of determining the settling rates of solids or particulate bearing liquids in a continuous process of a flowing stream wherein periodically a sample of the liquid is drawn into a transparent chamber through which a light beam is passed and detected after passing through the chamber and the liquid. The light transmissivity is measured at a number of different times. The light transmissivity of the chamber without liquid in it is also measured. The filling and emptying of the chamber is automatically controlled and the readings of the transmissivity are automatically obtained and stored from which storage means the partial settling rate as well as the full settling rate and the percentage of solids or part per million in the system can be ascertained. Thus, the invention provides an automatic simple apparatus and method for obtaining these readings.

Other objects, features and advantages of the invention will be readily apparent from the following description of certain preferred embodiments thereof taken in conjunction with the accompanying drawings although variations and modifications may be effected without departing from the spirit and scope of the novel concepts of the disclosure and in which:

DESCRIPTION OF THE PREFERRED EMBODIMENTS

Figure 1:
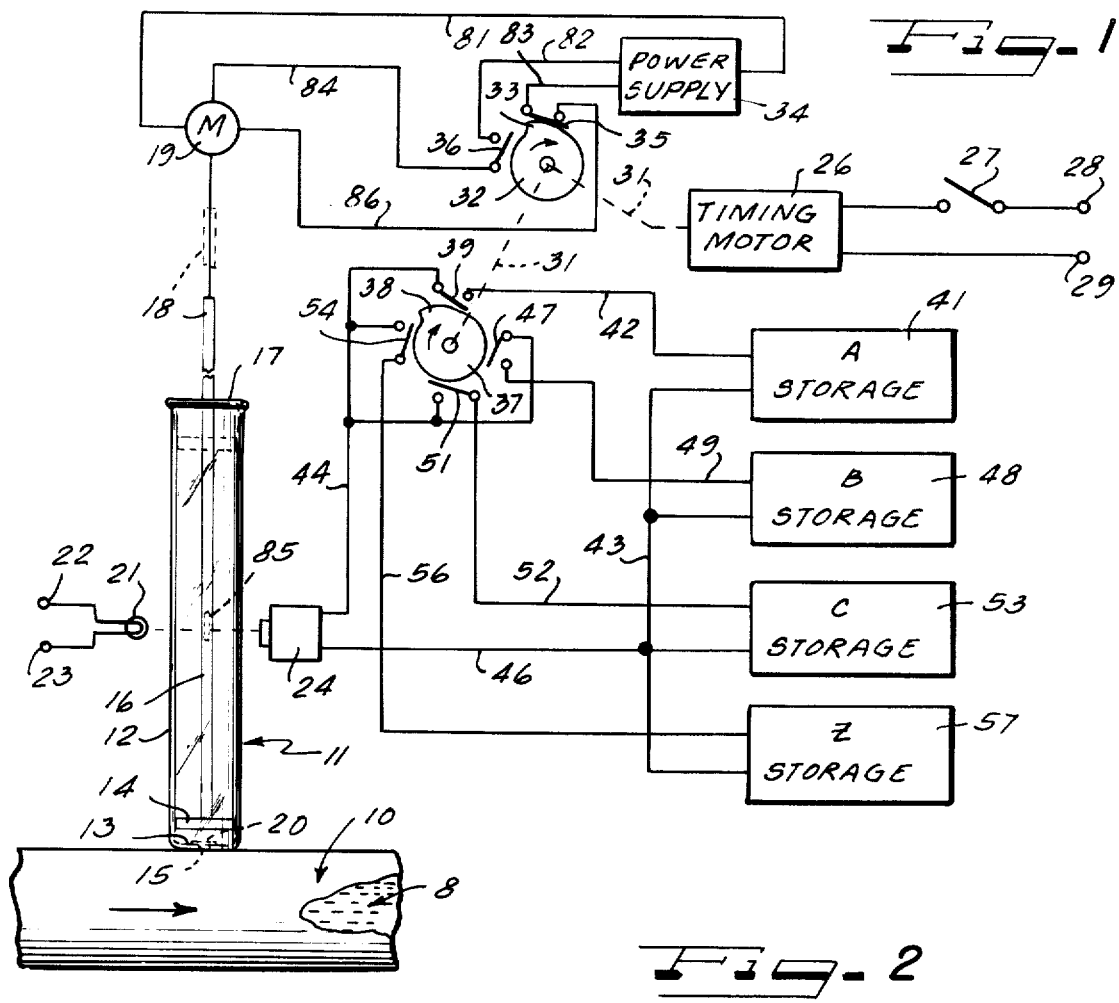
FIG. 1 is a block diagram illustrating the invention.

FIG. 1 illustrates a pipe 10 in which a liquid containing solid or particulate moves therethrough. A container or chamber 11 is attached to the pipe 10 and an opening 15 is provided for communication between the inside of pipe 10 and the container 11. A fluid 8 containing solids or particulate matter moves in pipe 10 and an analyzing chamber 11 is attached to the pipe 10 and communicates therewith with an orifice 15 over which a valve 20 is placed such that a piston 14 connected to a piston shaft 16 that extends to the end 17 of the chamber 16 can be moved to draw a sample of the liquid 8 into the chamber 11. A motor 19 is connected to the upper end 18 of the piston shaft 16 for actuating the piston 14 up and down in the chamber 11 to withdraw a sample into the container 11 and to exhaust it from the container 11 through the valve 20 back into the pipe 10. The walls 12 of the chamber 11 are transparent or at least a portion of the walls are transparent such that light from a light source 21 connected to a suitable power supply through terminals 22 and 23 will pass through the chamber 12 and the sample within the chamber to a light detector 24. A plurality of electrical storage signal devices 41, 48, 53 and 57 are connected to a common lead 43 which is connected by lead 46 to one side of the detector 24. The other side of the detector 24 is connected to a lead 44 which is connected to normally open contacts of a plurality of switches 39, 47, 51 and 54 mounted about a cam 37 which is driven by shaft 31 connected to the output of a timing motor 26. The cam 37 has a high portion 38 such that when the high portion is aligned with the switch 39 it moves its moveable contact into engagement with a stationary contact so that lead 44 is connected to lead 42 which is connected to the second side of the A storage means 41. The moveable contact of switch 47 when engaged by the high portion 38 of cam 37 connects lead 44 with lead 49 which is connected to the second side of B storage means 48. The moveable contact of switch 51 engages the fixed contact of the switch when the high portion 38 of cam 37 engages it so as to connect lead 44 to lead 52 which is connected to the second side of the C storage means 53. The moveable contact of switch 54 when engaged by the high portion 38 of cam 37 connects lead 44 to lead 56 which is connected to the second side of the Z storage 57.

The timing motor 26 also carries a cam 32 with a high portion 33 which is engageable with motor control switches 35 and 36 to energize the motor 19 which controls the piston 14 in the chamber 11. The power supply 34 has one side 81 connected to the motor 19 and a pair of outputs 82 and 83, respectively connected to fixed terminals of switches 35 and 36. The moveable contact of switch 35 is connected to lead 83 which is connected to the motor 19 when the switch 35 is closed and the lead 86 and lead 83 are electrically connected together such that the power supply 34 supplies power to the motor 19 to drive it in a first direction as, for example, to cause the piston 14 to move up in the chamber 11 to draw a sample from pipe 10 into the chamber 11. The switch 36 when closed by the high portion 33 of cam 32 connects power supply lead 82 to motor lead 84 so as to cause the motor 19 to drive in the opposite direction so as to move the piston 14 downwardly in the chamber 11 to eject the sample fluid back into the pipe 10.

The cams 32 and 37 are positioned on shaft 31 such that the high portions 33 and 38 of the cams 32 and 37, respectively, actuate the piston 14 and cause the light detector 24 to be connected to the storage means 41, 48, 53 and 57 in a sequence such that the first storage means receives a signal at time T0 which is very shortly after the container 11 has been filled with the sample fluid. The storage means 48 is connected by the switch 47 to the detector 24 at a subsequent time T1 which might, for example, be 30 seconds after the container 11 has been filled with sample material and during which time certain amount of settling of the particulate matter and solids will have occured so that more light will pass through the fluid at time T1 than it did at time T0. The storage means 53 is connected to the sampler 24 at a subsequent time T2 and the Z storage 57 is connected to the detector 24 after the plunger 14 has ejected the fluid from the chamber 11 and the detector 24 detects the light energy at a time when there is no fluid in the container. For this purpose, an opening 85 may be formed in the piston rod 16 so as to allow the light to pass from the light source 21 to the detector 24 when the piston 14 is in the down position illustrated in FIG. 1.

The detector 24 may be a photosensitive cell which produces an electrical output indicative of the amount of light energy which impinges upon it and this, of course, varies depending on the transmissivity of the container 11 and fluid contained in the container 11.

The sequence of operation is as follows:

1. The switch 27 is closed to start the sequence connecting power from power terminals 28 and 29 to timing motor 26 so that it starts and drives shaft 31 thus moving cams 32 and 37.
2. The sample is drawn into container 11 by the piston 14.
3. The light transmissivity is measured at time T0 (time 0) and is restored and held in the A storage 41. Reading A
4. A waiting period of precise time as for 0 to 30 seconds occurs.
5. The transmissivity is again measured and recorded and held in the storage 48. Time - T1, reading B
6. Wait a precise time as, for example, 0–60 seconds, at time T2.
7. Measure the transmissivity and store in the C storage 53.
8. Energize motor 19 so as to exhaust the sample from the container 11.
9. Read light transmissivity for calibration purposes with the container empty and store in Z storage 57. Z reading The cycle continues as long as switch 27 is closed.
The partial settling rate can be calculated as follows:

Partial settling rate $= A - B/T_1$

The full settling rate can be calculated as follows:

Full settling rate $= A - C/T_2$

The percentage solids or parts per million in the system can be calculated as $A - Z$.

Figure 2:
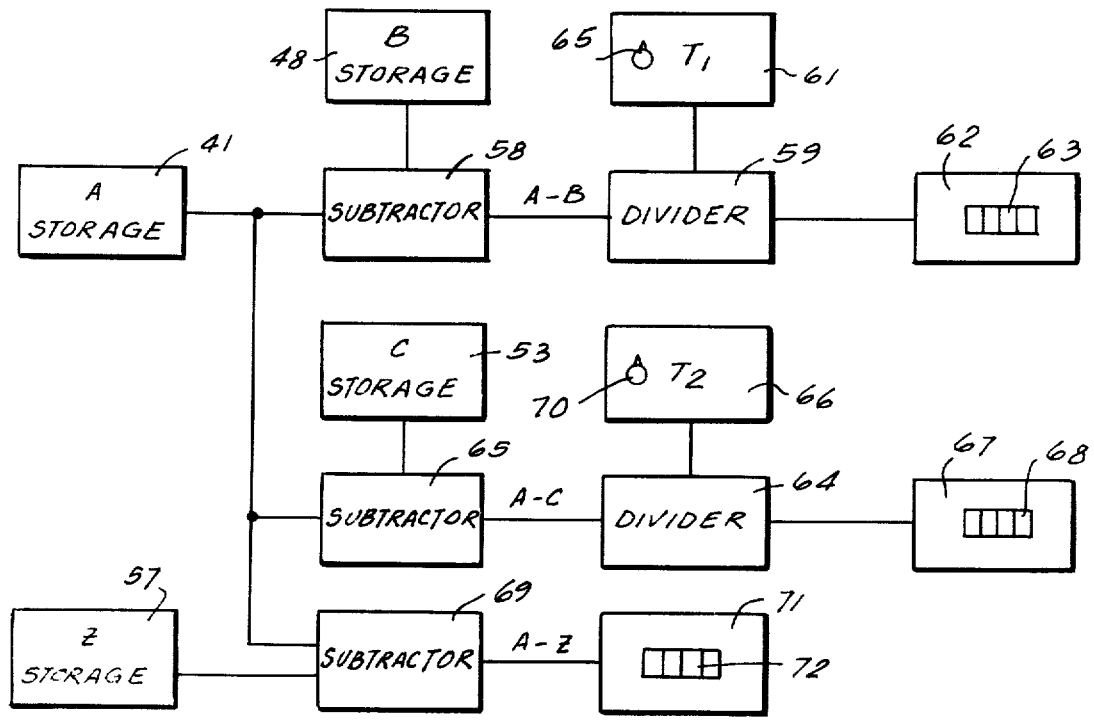
FIG. 2 is a block diagram illustrating the calculating portion of the invention.

These calculations can be performed with the apparatus illustrated in FIG. 2. The A storage 41 which retains the electrical signal proportional to the transmissivity at time $T_0$ when the sample is first placed into the chamber 11 is supplied to a subtraction circuit 58 which also receives an output from the B storage 48 in which the transmissivity of the sample and the container 11 has been measured at a time $T_1$ which might be approximately 30 seconds after time $T_0$. The output of the subtraction circuit 58 is equal to $A - B$ and this signal is supplied to a divider 59 which receives an input signal proportional to the time $T_1$ from a generator 61 which can be set manually or otherwise by a knob 65 to the time difference between the first transmissivity measurement which is supplied to A storage means 41 and the second transmissivity measurement which is supplied to B storage means 48. The electrical signal from the time generator 61 is supplied to the divider 59 wherein it is divided into the signals $A - B$ and this output is supplied to a meter 62 which indicates in its indicating portion 63 the partial settling rate of the solids or particulate in the sample in the container 11.

A subtraction circuit 65 also receives the output of the A storage 41 as well as an output from the C storage means 53 and subtracts C from A to produce an output signal $A - C$. A time generator 66 can be set by a knob 70 to time $T_2$ which is the time of the taking of the transmissivity which is supplied to the C storage 53 and which might be in the range of 60 seconds. A divider 64 receives the output of the subtraction circuit 65 and the output of the time generator 66 and the signal $A - C$ is divided by the time signal $T_2$ and the output is supplied to an indicator 67 which has an indicating portion 68 wherein the full settling rate of the solids or particulate in the sample in the chamber 11 is indicated.

The output of the Z storage 57 is supplied to a subtraction circuit 69 which also receives an output from the A storage means 41 and the output of the subtraction circuit 69 produce a signal $A - Z$ which is supplied to an indicator 71 that has an indicating portion 72 that indicates the percentage solids or part per million in the sample and the container 11.

It is seen that the present invention provides automatic simple means for calculating a partial settling rate, the full settling rate and the percentage of solids or part per million in the system and although the invention has been described with respect to preferred embodiments, it is not to be so limited as changes and modifications can be made therein which are within the full intended scope of the invention as defined by the appended claims.

I claim as my invention:

1. Apparatus for determining the settling rates of solids or particulate in moving liquid comprising a container fluidly communicating with said moving liquid, means for filing and emptying said container, motor means for controlling said filing and emptying means, transparent portions of side walls of said container, a light source mounted on one side of said container adjacent one of said transparent portions, a light sensor mounted on the opposite of said container adjacent the other transparent portion to measure light transmissivity, a timing motor connected to said motor means to cause it to fill and empty said container, a switch means connected to said timing motor and having a plurality of switches which are closed at different times by said timing motor, one side of said light sensor connected to one terminal of each of said plurality of switches, a plurality of storage means with first input terminals connected to the other side of said light sensor, a second terminal of each of said plurality of switches respectively connected to second input terminals of each of said plurality of storage means, a first subtractor receiving input signals from a first and a second of said plurality of storage means and subtracting said signals, a first time signal generator supplying an output signal proportional to the difference in times when the transmissivity signals were supplied to said first and second storage means, a first divider receiving the outputs of said first subtractor and said first time signal generator and dividing the subtractor signal by the time signal, and a first indicator receiving the output of said first divider to indicate the settling rate.

2. Apparatus according to claim 1 wherein said timing motor includes a pair of cams which engage said plurality of switches to open and close them in a predetermined sequence.

3. Apparatus according to claim 1 including second subtractor means receiving input signals from said first and a third of said plurality of storage means and subtracting said signals, a second time signal generator supplying an output signal proportional to the difference in times between when the transmissivity signals where supplied to said first and third storage means, a second divider receiving the outputs of said second subtractor and said second time signal generator and dividing the subtractor signal by the time signal, and a second indicator receiving the output of said second divider to indicate the final settling rate.

4. Apparatus for determining the settling rates of solids or particulate in liquid, comprising a container in which a sample of said liquid can be held, a means for measuring to obtain a light transmissivity signal of said sample at a first time, a timing means connected to said means for measuring to obtain a light transmissivity of said sample at a second time, means for calculating the settling rate of solids connected to said means for measuring, wherein said container is transparent to light energy and said means for calculating includes first means for storing said light transmissivity signal at said first time, wherein said means for calculating includes second means for storing said light transmissivity signal at said second time, a subtractor connected to said first and second storage means, a time signal generator for producing a signal proportional to the time difference between said first and second times, a divider means receiving the outputs of said subtractor and said time signal generator and dividing the time signal generator signal into the signal from said subtractor and indicator means receiving the output of said divider means to indicate the settling rate, wherein said measuring means includes a light source mounted on one side of said container and a light detector mounted on the other side of said container, wherein said timing means controls said measuring means to obtain a light transmissivity signal of said sample at a third time, and said calculating means includes a third storing means for storing said light transmissivity signal at said third time, a second time signal generator for producing a signal proportional to the time difference between said first and third times, a second subtractor connected to said first and second storage means and producing a difference signal, a second divider means receiving inputs from said second subtractor and said second time signal generator and dividing the second time generator signal into the output of said second subtractor and second indicator means connected to the output of said second divider means and indicating a full settling rate, and including a fourth storing means for storing a light transmissivity signal when there is no sample in said container, a third subtractor receiving inputs from said first and fourth storage means and producing a difference signal, and a third indicator connected to said third subtractor and indicating the percentage of solids or parts per million of solids.

5. Apparatus for determining the settling rates of solids or particulate in liquid, comprising a container in which a sample of said liquid can be held, a means for measuring to obtain a light transmissivity signal of said sample at a first time, a timing means connected to said means for measuring to obtain a light transmissivity of said sample at a second time, means for calculating the settling rate of solids connected to said means for measuring, wherein said container is transparent to light energy and said means for calculating includes first means for storing said light transmissivity signal at said first time, and wherein said means for calculating includes second means for storing said light transmissivity signal at said second time, a subtractor connected to said first and second storage means, a time signal generator for producing a signal proportional to the time difference between said first and second times, a divider means receiving the outputs of said subtractor and said time signal generator and dividing the time signal generator signal into the signal from said subtractor and indicator means receiving the output of said divider means to indicate the settling rate, wherein said measuring means includes a light source mounted on one side of said container and a light detector mounted on the other side of said container, said timing means controlling said measuring means to obtain a light transmissivity signal of said sample at a third time, and said calculating means including a third storing means for storing said light transmissivity signal at said third time, a second time signal generator for producing a signal proportional to the time difference between said first and third times, a second subtractor connected to said first and second storage means and producing a difference signal, a second divider means receiving inputs from said second subtractor and said second time signal generator and dividing the second time generator signal into the output of said second subtractor and second indicator means connected to the output of said second divider means and indicating a full settling rate.

6. Apparatus for determining the settling rates of solids or particulate in liquid, comprising a container in which a sample of said liquid can be held, a means for measuring to obtain a light transmissivity signal of said sample at a first time, a timing means connected to said means for measuring to obtain a light transmissivity of said sample at a second time, means for calculating the settling rate of solids connected to said means for measuring, wherein said container is transparent to light energy and said means for calculating includes first means for storing said light transmissivity signal at said first time, and wherein said means for calculating includes second means for storing said light transmissivity signal at said second time, a subtractor connected to said first and second storage means, a time signal generator for producing a signal proportional to the time difference between said first and second times, a divider means receiving the outputs of said subtractor and said time signal generator and dividing the time signal generator signal into the signal from said subtractor and indicator means receiving the output of said divider means to indicate the settling rate, and wherein said measuring means includes a light source mounted on one side of said container and a light detector mounted on the other side of said container.

* * * * *